United States Patent
Lerner

(10) Patent No.: US 10,127,350 B2
(45) Date of Patent: Nov. 13, 2018

(54) DECONSTRUCTING OVERLAPPED PEAKS IN DROPLET DIGITAL POLYMERASE CHAIN REACTION DATA

(71) Applicant: Bio-Rad Laboratories, Inc., Hercules, CA (US)

(72) Inventor: Jeffrey Lerner, Walnut Creek, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 595 days.

(21) Appl. No.: 14/790,810

(22) Filed: Jul. 2, 2015

(65) Prior Publication Data

US 2016/0004815 A1 Jan. 7, 2016

Related U.S. Application Data

(60) Provisional application No. 62/020,783, filed on Jul. 3, 2014.

(51) Int. Cl.
*G06F 19/22* (2011.01)

(52) U.S. Cl.
CPC .................... *G06F 19/22* (2013.01)

(58) Field of Classification Search
None
See application file for complete search history.

(56) References Cited

U.S. PATENT DOCUMENTS

| | | |
|---|---|---|
| 8,457,440 B1 | 6/2013 | Johnson et al. |
| 2005/0021244 A1 | 1/2005 | Nicoli et al. |
| 2009/0228245 A1 | 9/2009 | Gilbert et al. |
| 2012/0051549 A1 | 3/2012 | Nagel et al. |

OTHER PUBLICATIONS

Baker, "Digital PCR hits its stride," Nature Methods, vol. 9(6), p. 541-544, 2012.*
PCT/US2015/039039 , "International Search Report and Written Opinion", dated Sep. 30, 2015, 11 pages.
"The one and only Oxford Nanopore talk at AGBT 2014—with real data" posted on Feb. 14, 2014 accessed on the internet at: http://flxlexblog.wordpress.com/2014/02/14/the-one-and-only-oxford-nanopore-talk-at-agbt-2014-with-real-data/.
Extended European Search Report from EP 15815266.0 dated Feb. 1, 2018; 10 pages.

\* cited by examiner

*Primary Examiner* — G Steven Vanni
(74) *Attorney, Agent, or Firm* — Kilpatrick Townsend and Stockton LLP

(57) ABSTRACT

To determine a peak signal corresponding to a particular part of a sample, a data signal for a cluster can be transformed into a set of localized functions. For example, the data signal can be transformed to obtain coefficients of a set of wavelets, which can span a variety of scales that define an exponential decay of the wavelet. The coefficients in a time region for which a peak signal is to be obtained can be replaced with coefficients that model the behavior of tails of other peaks. The tail model can be determined using nonlinear regression, which may need to only be performed once. An inverse transform can then provide a background signal that can be subtracted from the input data signal to provide the desired peak signal.

20 Claims, 12 Drawing Sheets
(8 of 12 Drawing Sheet(s) Filed in Color)

US 10,127,350 B2

DECONSTRUCTING OVERLAPPED PEAKS IN DROPLET DIGITAL POLYMERASE CHAIN REACTION DATA

CLAIM OF PRIORITY

The present application claims priority from and is a non-provisional application of U.S. Provisional Application No. 62/020,783, entitled "Deconstructing Overlapped Peaks", filed Jul. 3, 2014, the entire contents of which is herein incorporated by reference for all purposes.

BACKGROUND

In droplet digital polymerase chain reaction (ddPCR), droplets pass by a sensor that detects whether a droplet includes a particular template nucleic acid sequence (e.g., DNA or RNA). As the droplets move by the sensor in time, a data signal is obtained. The signals from multiple droplets may overlap with each other, which can cause problems in determining a property of a particular droplet. Often, such droplets with overlapping signals are discarded.

Data in a series often consists of amplitude peaks, which may or may not be separated by some region of baseline level. If they are separated, they can usually be modeled by some function and analyzed by nonlinear regression or analyzed by peak identification methods, such as locating the extrema and associating peaks and troughs with peak locations and peak boundaries. When the peaks become close enough to overlap, this can become difficult to analyze since not only do the peaks occlude each other, they actually lift the adjacent peaks making it difficult to determine the appropriate baseline for the peak. Furthermore, if there are many peaks, typical regression methods may fail to converge. And, such regression methods require extracting all of the component peaks in order to examine any single peak. The performance cost from this may be prohibitive.

BRIEF SUMMARY

Embodiments can provide systems, methods, and apparatuses for determining a signal from a particular part of a sample, where signals from various parts of the sample overlap with each other. For example, to determine a peak signal corresponding to a particular part of a sample, a data signal for a cluster can be transformed into a set of localized functions. For example, the data signal can be transformed to obtain coefficients of a set of wavelets, which can span a variety of scales that define an exponential decay of the wavelet. The coefficients in a time region for which a peak signal is to be obtained can be replaced with coefficients that model the behavior of tails of other peaks. The tail model can be determined using nonlinear regression, which may need to only be performed once. An inverse transform can then provide a background signal that can be subtracted from the input data signal to provide the desired peak signal. The resulting peak signal can have any form, and not necessarily the form of a particular model for the peak.

Other embodiments are directed to systems and computer readable media associated with methods described herein.

A better understanding of the nature and advantages of embodiments of the present invention may be gained with reference to the following detailed description and the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DEFINITIONS

Figure 1A:
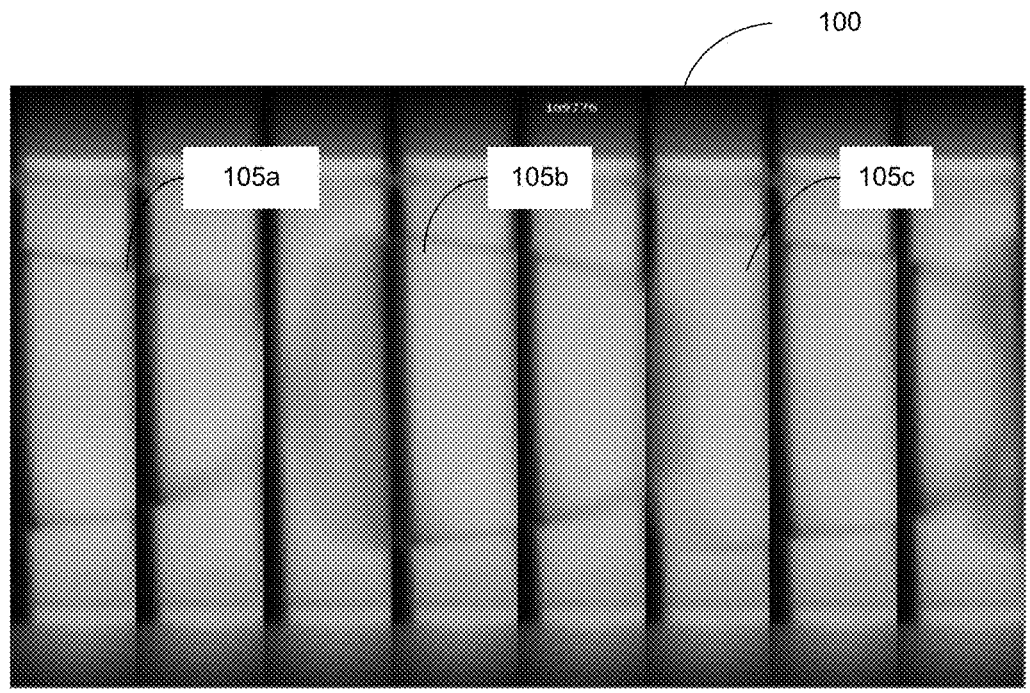
FIG. 1A is a diagram 100 showing droplets passing through a tube.

A sample can be a specific molecule (e.g., a polynucleotide, such as a DNA molecule) or be a mixture composed of many molecules of different types. Molecules of the same type can be extracted from the mixture (e.g., by chromatography) at different times. For example, a plurality of droplets of a sample can be analyzed as they move through a channel. Thus, different parts of the sample can provide different signals at different times, where the signals may overlap.

A data signal can correspond to a measurement of any physical quantity over a period of time. The data signal can correspond to a plurality of parts of the sample. A peak signal is a signal from a part of the sample, e.g., a particular droplet of the sample. The data signal can be composed of a plurality of peak signals when the peak signals overlap with each other. A cluster refers to a group of peak signals that overlap with each other.

DETAILED DESCRIPTION

In certain experiments, signals from different parts of a sample can interfere with each other. For example, signals from different droplets in droplet digital polymerase chain reaction (ddPCR) can interfere with each other when the droplets stick to each other. It can be difficult to identify a particular peak in a cluster of peaks, e.g., a cluster corresponding to a group of droplets.

To determine a peak signal corresponding to a particular part of a sample, embodiments can transform a data signal for the cluster in a set of localized functions. For example, the data signal can be transformed to obtain coefficients of a set of wavelets, which can span a variety of scales that define an exponential decay of the wavelet. The coefficients in a time region for which a peak signal is to be obtained can be replaced with coefficients that model the behavior of tails of other peaks. The tail model can be determined using nonlinear regression, which may need to only be performed once. An inverse transform can then provide a background signal that can be subtracted from the input data signal to provide the desired peak signal. The resulting peak signal can have any form, and not necessarily the form of a particular model for the peak.

I. Data

Droplet Digital PCR (ddPCR) is one measurement process where overlapping data peaks can be seen. These clustered droplets in ddPCR data streams can be difficult to analyze due to the overlapping signals. Examples of other types of data with the same problem include data streams from sequencing (e.g., nanopore sequencing), melt peaks in qPCR (Quantitative real-time PCR), and chromatography. Such examples also involve a data stream where signals from different parts of a sample are close to each other in time. A problem is how to separate the signals so that a specific signal can be attributed to a particular part of the sample. Thus, although some examples refer to ddPCR, such discussions or parts of such discussions are applicable to other techniques.

The different parts of the sample could be different droplets, as with ddPCR. In another example, a different part of a sample can correspond to a different base in a DNA molecule. The DNA molecule can move across a sensor that obtains a signal for each base. These signals can overlap in time. For chromatography, the different part of the sample can correspond to different molecules sample that elute at different times.

FIG. 1A is a diagram 100 showing droplets passing through a tube. Three droplets 105a, 105b, and 105c are shown. These droplets are generated in ddPCR. Each droplet might contain and provide copies of a particular DNA sequence, which can be labeled with fluorescent probe. If light is emitted from a droplet, a detector (e.g., a cytometer) can detect the light and generate a data signal. Each droplet can be spiked with a dye such that a background signal can identify droplets without a signal.

Figure 1B:
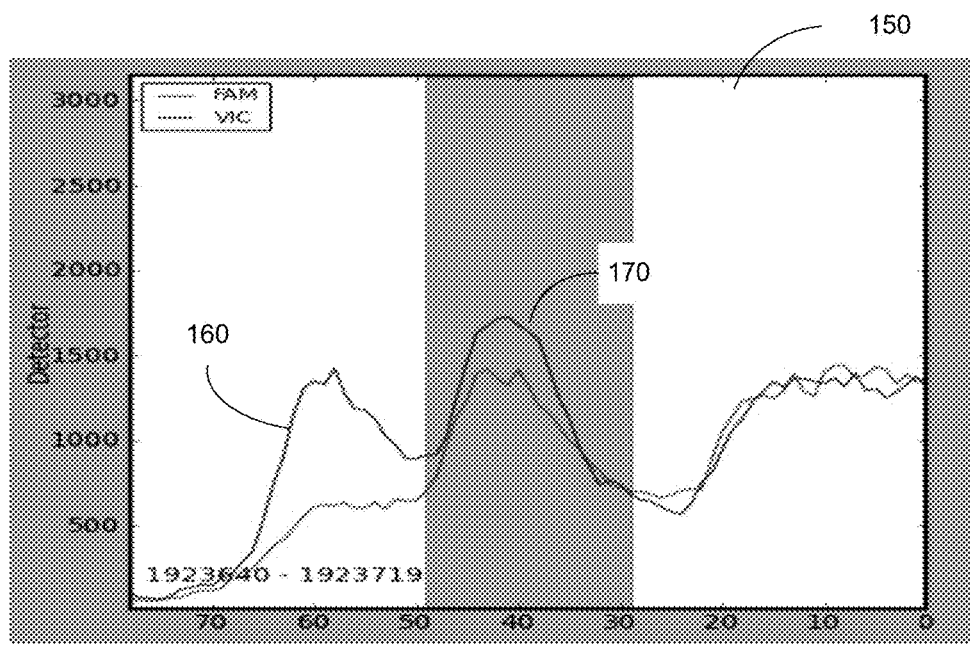
FIG. 1B us a diagram 150 showing a data signal generated from the droplets in FIG. 1A.

FIG. 1B us a diagram 150 showing a data signal 160 generated from the droplets in FIG. 1A. Time is on the horizontal axis. The strength of the detector signal is on the vertical axis. As shown, peaks correspond to different droplets. The two signals FAM and VIC correspond to different fluorescent dyes, which would correspond to different template DNA molecules (e.g., once of different sequences). For other applications, each peak could correspond to a signal from a different base on a sequence.

In ddPCR, the sample is partitioned with regions into respective droplets, which act as reaction chambers. Ideally, the partitioning is such that only one template DNA molecule is in a droplet. If a droplet includes a template DNA molecule, the template can be amplified to provide a sufficient amount of template DNA for generating a signal. In FIG. 1B, the droplet passing by the detector between about 30 and 50 time units appears to generate a signal for both template DNA molecules. The number of positive droplets showing a signal for a particular template DNA can be counted to determine an amount of template DNA in the sample, modulo Poisson correction for multiple templates in a single droplet. Thus, one can get a percentage of all droplets that have a particular sequence. This digital content of droplets provides advantages over qPCR.

The total number of droplets can be determined from all of the droplets that are positive for any of the template sequences, and determine from negative droplets, which may have a small but detectable signal (e.g., the signal may be below a threshold for positively indicating the existence of a template DNA molecule). In other implementations, a different labeled probe can be used to detect droplets that don't include the template DNA of interest. Using such a second probe can allow one to detect all the droplets, even when some do not include the template of interest. Thus, an accurate percentage of droplets that include the template of interest can be determined.

As one can see visually, data signal 160 has a peak 170. But, the width of the data signal might be large as the data signal is above 500 for more than 60 seconds. Thus, data signal 160 might be discarded for being too wide, and incapable of being analyzed. A further discussion of overlapping of data peals is now provided.

II. Data Peaks

The peaks in a data signal corresponding to different parts of the sample can at different relationships to each other. Namely, some peaks can be close to each other, overlap with each other, or be separated from other peaks. For example, droplets in ddPCR can stretch and/or stick to each other due to complicated fluidics and due to a specific technique in the creation of the droplets (e.g., skinless droplets may be more likely to stick to each other).

Herein, we define three classes of peaks. (1) Isolated: No overlap with significant spacing between peaks. Each peak drops down to the baseline level. (2) Separable: Pairs or small numbers of peaks are close but not too close, whereby peak/trough analysis may suffice or multi-peak nonlinear regression may converge, albeit slowly. Regions between adjacent peaks do not drop down to the baseline. (3) Overlapped: It is difficult to determine what separates peaks because the overlap is so large. There is no rigorous definition of the demarcation line between the regimes, but it is clear by observation. An example of this set is shown below.

Figure 2:
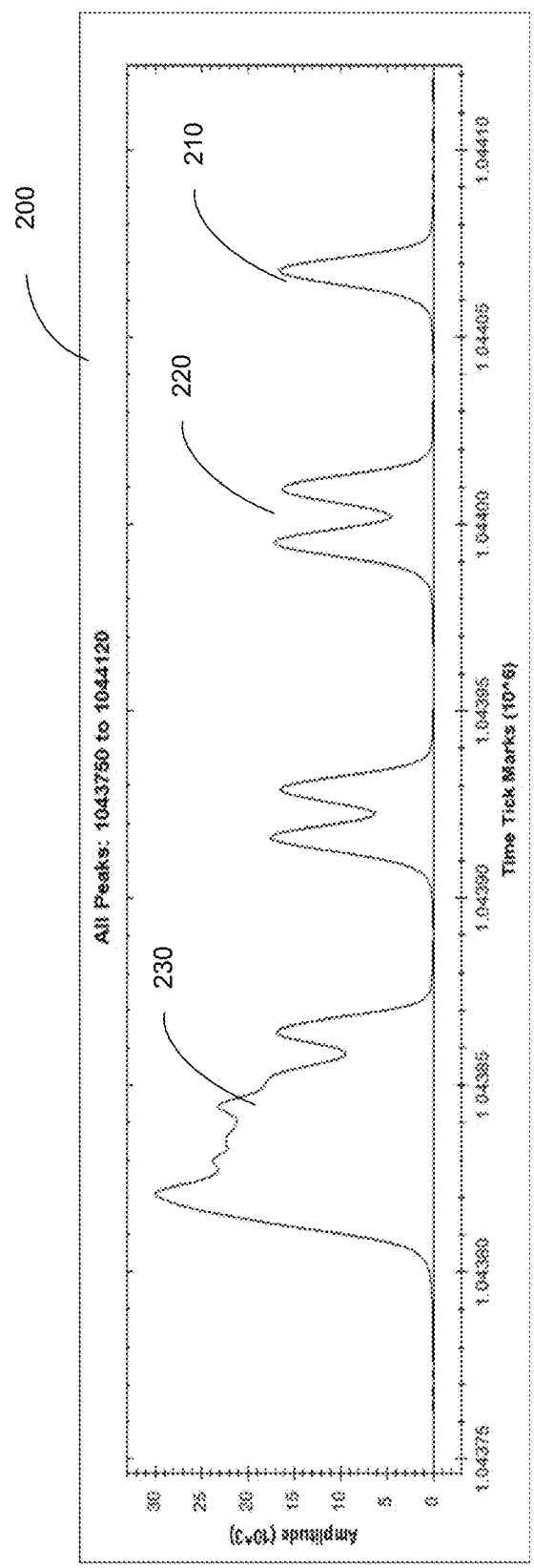
FIG. 2 is a plot 200 of various classes of peaks that can occur in a data signal.

FIG. 2 is a plot 200 of various classes of peaks that can occur in a data signal. For ddPCR, each peak can correspond to a different droplet. Some droplets are near other droplets when passing through a cytometer, and thus a signal from one droplet can overlap with a signal of another droplet. Also, droplets can stick to each other and form a cluster of droplets. The peaks can correspond to a same color (fluor). Or, the data can be a sum of all signals (e.g., of the different colors).

Peak 210 is isolated (class 1) and can be analyzed using a model-based (e.g., Gaussian) single peak nonlinear regression. Such a class of peaks is easy to identify. Cluster 220 of two peaks corresponds to class 2. These peaks are overlapping, but can be separable using a model-based (e.g., Gaussian) multipeak nonlinear-regression.

Cluster 230 corresponds to class 3, where the amount of overlap is large. When the overlap is large, the height of peaks can be increased significantly from the tails of other peaks. Further, in the case of ddPCR, the droplets can stick to each other, which can cause the signal from a particular droplet to change due to the physical interaction of the droplets.

Typically, the data signal for such a cluster (also called a glob, globule, or globlet) is currently discarded in many applications as there is no method that effectively can analyze this case. For example, globules can be removed if the width is too large (e.g., based on sum of all signals). But, this discards data, which can be particularly problematic when one is trying to identify rare events. These are typically discarded in analysis as there is no method that can effectively analyze this case. Embodiments provide techniques for identifying a peak signal corresponding to a particular part of the sample in a globule of peaks, e.g., as shown in cluster 230.

In some instances, one can discard globs of droplets and single droplets based on width, and it does not matter because the same number of negative and positive droplets are discarded. Since the ratio of the positive to negative droplets is typically desired, the ratio is not significantly changed as the numbers of positive and negative droplets are about equal. But there are rare events, where discarding individual droplets matters. Or, if you have very high loading (i.e., many droplets with multiple templates), then your individual droplets can also matter.

Modeling peaks in class 3 with nonlinear regression can be problematic, as the close proximity can induce severe distortion in shape. Multi-peak nonlinear regression may have many parameters with low probability of convergence for >=3 peaks. Adjacent overlapped peaks lift each other causing a distortion in the amplitude due to a baseline shift. Such modeling can fail to represent the distortion. Another problem is that multi-peak regression requires solving for all of the peaks in order to obtain any single peak, whereas it can be desirable to extract a particular peak. Peak analysis often requires magic numbers which are not intrinsic to the problem. Further, different peaks may require different models. And, nonlinear regression can be slow due to the computational complexity.

In order to avoid the above problems, some embodiments use intrinsic properties. For example, embodiments can use the range of scales present in the data (e.g., obtained via frequency analysis in a data signal) or relative locations of peaks. Embodiments can use these properties to obtain a particular peak signal and the resulting background signal. Embodiments can separate out peaks of extremely complex shape, which cannot be modeled, from heavily overlapped data.

III. Method

As mentioned above, it can be difficult to identify a particular peak in a cluster of peaks. To determine a peak signal corresponding to a particular part of a sample, embodiments can transform a data signal for the cluster in a set of localized functions. For example, the data signal can be transformed to obtain coefficients of a set of wavelets, which can span a variety of scales that define an exponential decay of the wavelet. The coefficients in a time region for which a peak signal is to be obtained can be replaced with coefficients that model the behavior of tails of other peaks. The tail model can be determined using nonlinear regression, which may need to only be performed once. An inverse transform can then provide a background signal that can be subtracted from the input data signal to provide the desired peak signal. The resulting peak signal can have any form, and not necessarily the form of a particular model for the peak.

Figure 3:
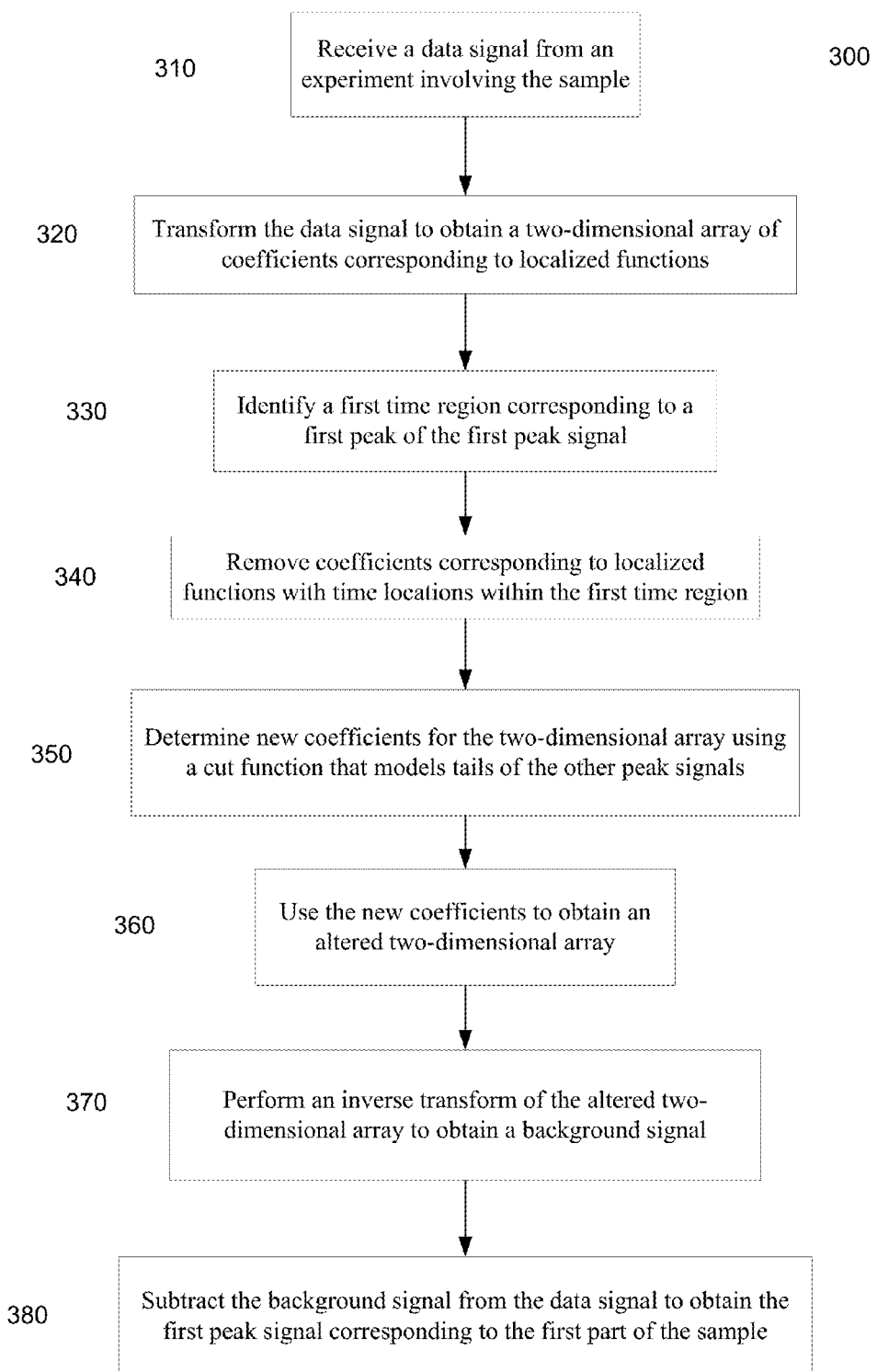
FIG. 3 is a flowchart of a method 300 of identifying a first peak signal according to embodiments of the present invention.

FIG. 3 is a flowchart of a method 300 of identifying a first peak signal according to embodiments of the present invention. The first peak signal corresponds to a first part of a sample from among other peak signals of other parts of the sample. The first peak can be any peak, as the term first simply refers to a particular peak. Method 300 can be partly or wholly performed by a computer system.

At block 310, a data signal from an experiment involving the sample is received. The data signal has an amplitude that varies over time. The data signal corresponds to many peak signals. For example, the data signal can correspond to multiple droplets, bases on a nucleic acid, amino acids of a protein, or other parts of a molecule. A signal from the sample can be obtained at various times, e.g., at periodic times. Given that the data signal corresponds to multiple parts of a sample, the data signal comprises a plurality of overlapped peaks at different times. The experiment can be a droplet digital PCR experiment, where the sample includes a plurality of droplets containing nucleic acids. The plurality of droplets can correspond to different parts of the sample.

In one embodiment, a width of the data signal can be used to determine a type of analysis to be performed. For example, data signal with a large width can be analyzed using method 300. Single peaks (e.g., data signals with a small width) can be analyzed using other techniques, such as regression.

The data signal can be of just one color or a sum of the signals for several colors (e.g., all colors). Embodiments can further use the sum first (e.g., to determine a cluster of peaks for using method 300), and then later using the signal for each color in method 300.

At block 320, the data signal is transformed to obtain a two-dimensional array of coefficients corresponding to localized functions. Each coefficient corresponds to a localized function having a time location and a scale factor. The time locations of the localized functions can correspond to the times at which the data signal is obtained.

The different time locations allow modeling the peak of interest regardless of where the peak is located. The scale factor can correspond to a period (or corresponding variable, such as frequency) of the localized function. For example, wavelets of different period will have different widths in time. Using wavelets of different scale factor at the same time location provides greater accuracy in representing the data signal. The number of scale factors to use can be determined based on the values of the resulting coefficients. For example, once the coefficients become small enough (e.g., less than a threshold), then a maximum scale factor can be determined for all locations.

The transformation can include taking a convolution of the data signal with the set of localized functions. For example, a convolution of the data signal can be taken with a particular localized function (i.e., unique pair of time location and scale factor), which may be centered at a time t and having a scale factor a. This convolution with the particular location function provides a matrix element in the 2D array. Thus, such a convolution can provide a particular coefficient corresponding to the particular localized function.

In one embodiment, the convolution can be determined using a discrete Fourier transform (e.g., FFTs) or other numerical technique that integrates over a finite domain. A different numerical technique can include an interpolation between the data points of the signal within a finite boundary (e.g., assuming that the data signal is zero before and after the cluster of overlapping peaks). The area between the data points of the signal can then be determined using the interpolated function. Accordingly, the computing the convolution can include: calculating a first discrete transform of the data signal to obtain a first set of data points; calculating a second discrete transform of the particular localized function to obtain a second set of data points; and multiplying data points of the first set with corresponding data points of the second set and summing to obtain a result of the convolution.

At block 330, a first time region corresponding to a first peak of the first peak signal is identified. The first time region corresponds to a time for which the first peak signal is to be determined. Such a time region can be determined in various ways. For example, the minima between the peaks can be identified. A local minimum between the first peak and a second peak can be identified as a first boundary of the first time region. In another example, when the peak is an end peak, a minimum between a neighboring peak can be identified, and the distance from the minimum to a maximum can be determined. The distance can be used to determine the end of the time region such that it is symmetric about the maximum within the time region.

At block 340, the coefficients of the two-dimensional array corresponding to localized functions with time locations within the first time region are removed. These coefficients can be primarily associated with the first peak signal. Thus, coefficients of the first peak signal are being removed to obtain a background signal, which can be subtracted from the data signal to obtain the first peak signal.

The removed coefficients can correspond to only part of the range of scale values. For example, the range can be where the coefficients have the largest value. Values that are small have little effect and thus can be left as is, or ignored in later parts of the calculation.

At block 350, new coefficients for the two-dimensional array are determined using a cut function that models tails of the other peak signals. The cut function can receive as input a particular time and scale value and provide a value for a particular coefficient of the 2D array. The cut function models the tails of the other peaks within the first time region. As the other peaks will contribute tails to the first time region due to the overlap, the effects of the other peaks should not be ignored. Thus, the cut function can provide an accurate representation (i.e., in the space of the localized functions) of how the adjacent peaks decay into the first time region. In one embodiment, the cut function can be computed once, and then used for analysis of any data signal. An example of a cut function is provided below.

At block 360, the new coefficients are used to obtain an altered two-dimensional array. For example, the new coefficients can be inserted into the 2D array in the first time region (and any selected range for the scale values). The altered 2D array now represents the background signal (i.e., data signal for the other peaks in the cluster) in the space of the localized functions.

At block 370, an inverse transform of the altered two-dimensional array is performed to obtain a background signal. The inverse transform can be obtained at a particular time location by summing (e.g., via an integral) over the coefficients corresponding to the particular time location. The inverse transform can be determined by numerically solving a convolution integral (e.g., using FFT or other discrete transform) for each scale value. The results of all scale values at the particular time location can then be summed. In one embodiment, the numerical integration technique used for the transform can also be used for the inverse transform. For example, FFTs can be used for determining the integrals in both transforms.

At block 380, the background signal can be subtracted from the data signal to obtain the first peak signal (e.g., a recovered peak) corresponding to the first part of the sample. Since the background signal corresponds to the other peaks (i.e., besides the first peak) and the data signal corresponds to all peaks of the cluster, the result of the subtraction can provide the first peak.

In this manner, the peak of interest can be obtained. The result is plausible, and example below can show that the data peaks are not Gaussian, and thus plausible for the physical effects of clustering that cause the peak signal to change from the Gaussian shape of isolated peaks.

IV. Representation in Localized Functions

As mentioned above, an embodiment can take the data signal for a cluster of peaks and transform the data signal into a representation of a set of localized functions. The set of localized functions are centered at different locations and have different scale factors, i.e., each localized function has a unique pair of scale factor and location. The transform can use the localized functions as basis functions for depicting the data signal. The representation can include a sufficient number of localized functions that one does not perform regression to determine coefficients of the localized functions, but instead the coefficients are determined from integrals.

A. Transform

In one embodiment, the transform can be obtained via the equation:

$$\tilde{u}(a, t) = \int_{-\infty}^{\infty} \left[ u(t') \frac{1}{\sqrt{a}} \psi^* \left( \frac{t-t'}{a} \right) \right] dt'. \quad (1)$$

The variable u(t') is the signal to be analyzed, and ψ( ) corresponds to the localized basis functions. The transform provides a particular coefficient of the two-dimensional array ũ of coefficients. Each value of a and t correspond to a different coefficient. The integral involves the data signal u(t) and a particular localized function that has a scale factor a and is centered at time t. The integral is over time t' and provides a measure of how much of the data signal u(t') is represented by the particular localized function centered at time t. A next coefficient can be obtained by changing the scale a or the time t.

In this manner, the 2D array of coefficients can be determined for the space defined by a range of scales and time. The input can correspond to a one dimensional signal, e.g., a signal value for each of a plurality of sampling times. The integral can be over these sample times, and may be done numerically.

The coefficients of the 2D array and the set of location functions provide a linear sum that is equivalent to the input data signal. Thus, the input data signal is expressed as a superposition of localized basis functions, each of which has a given location and scale. The location determines where the localized function is centered, which in this case is t. The scale provides how quickly the localized function decays, and thus can provide a length associated with a particular function. The 2D array can correspond to a matrix of different times and scales. For each time and each scale (e.g., period), there is an amplitude associated with it.

Figures 4A, 4B:
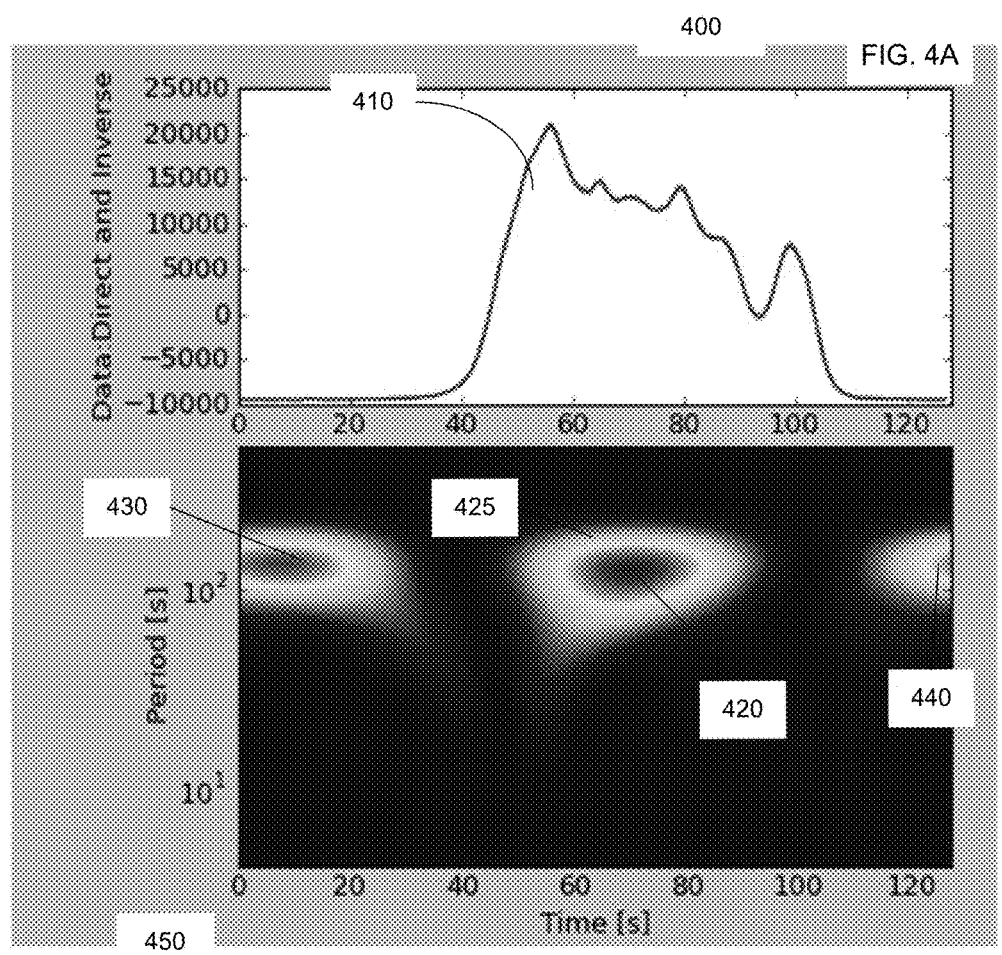
FIG. 4A shows a plot 400 of a cluster 410 of peaks in a data signal taken over a period of time according to embodiments of the present invention.
FIG. 4B shows a heat map 450 of a 2D array of coefficients of localized functions determined from an input data signal according to embodiments of the present invention.

FIG. 4A shows a plot 400 of a cluster 410 of peaks in a data signal taken over a period of time according to embodiments of the present invention. The horizontal axis is time, and the vertical axis is amplitude of the data signal. Cluster 410 is shown between about 35 and 115 seconds. Cluster 410 corresponds to a plurality of droplets.

FIG. 4B shows a heat map 450 of a 2D array of coefficients of localized functions determined from an input data signal according to embodiments of the present invention. The horizontal axis is time (same as in FIG. 4A), and the vertical axis is period (an example scale).

The localized functions having a period below 10 and above about 300 have small amplitudes for the coefficients. The highest amplitudes are shown with reference level 420 in a subset 425 of coefficients. This 2D array (matrix) defines the input data signal in the space of the localized functions and can be used to define the background signal, which in turn can be used to determine a particular peak signal.

Heat map 450 also shows appreciable coefficients for times of 0 seconds to about 23 seconds (subset 430), and for greater than about 118 seconds (subset 440). These two subsets have large values as a result of using wavelets that have an average value of zero. Thus, the localized functions in the time regions corresponding to subsets 430 and 440 cancel out the negative effects from the localized functions for subset 425.

B. Localized Functions (Wavelets)

Various localized functions can be used that combine scale with a location (e.g., functions that do not have an average value of zero). The localized function can be selected to represent the tails of adjacent peaks. One type of signal analysis that combines scale with location/region is wavelet analysis. The input signal can be expresses as a sum of wavelet functions. A wavelet function is characterized by unique scale and unique location.

In one embodiment, the localized functions can satisfy an admissibility constraint. The admissibility constraint can be defined as:

$$c_\psi = \int_0^\infty |\hat{\psi}(\omega)|^2 \frac{d\omega}{|\omega|} < \infty \tag{2}$$

The caret over the function $\hat{\psi}$ signifies a Fourier transform.

Given the constraint that the integral of a basis function is finite constrains the basis function to be localized, i.e., decay sufficiently fast. The constraint can be a condition for a zero mean (i.e., integral is zero), as is the case for a sinusoidal wave. For a zero mean condition, it effectively requires that the zero frequency Fourier transform component equals zero. The admissibility constrain can ensure that a transform and inverse transform can be performed.

Accordingly, the localized functions can be selected such that an inverse transform can be performed. The inverse transform can be defined as follows:

$$u(t) = \frac{1}{c_\psi} \int_{-\infty}^\infty \int_0^\infty \left[ \tilde{u}(a, t') \frac{1}{\sqrt{a}} \psi\left(\frac{t-t'}{a}\right) \right] \frac{da}{a^2} dt' \tag{3}$$

There are many types of wavelet analysis: Two examples are: discrete wavelet transform (DWT) and continuous wavelet transform (CWT). The DWT has basis elements that are defined numerically via recursion relations.

The CWT has a unique advantage in that one can choose a wide variety of basis elements subject to fairly weak constraints (e.g., admissibility constraint), which can allow one the freedom to choose functions that are appropriate to the physics of the problem at hand. CWT is used in the examples below.

In one implementation, the Mexican Hat Wavelet is used, which is define by:

$$\psi(t) = \frac{2}{\sqrt{3\sigma\pi^{\frac{1}{4}}}} \left(1 - \frac{t^2}{\sigma^2}\right) e^{\frac{-t^2}{2\sigma^2}} \tag{4}$$

This wavelet is chosen because it can reasonably model the behavior of adjacent tails of neighboring peaks. The Gaussian shape for the background tails is known from single peak analysis to be appropriate and is reasonable to model the tails of peaks. Thus, the coefficients for the cut time range can be replaced with other coefficients that can model the tails of the other peaks. And, at the same time, the wavelet can model peaks as well. Given that the functions can be used to model the tails, the functions can be used to model the background of the overlapped peak relative to the selected peak. The recovered peak of the droplet can have any shape.

Figure 5:
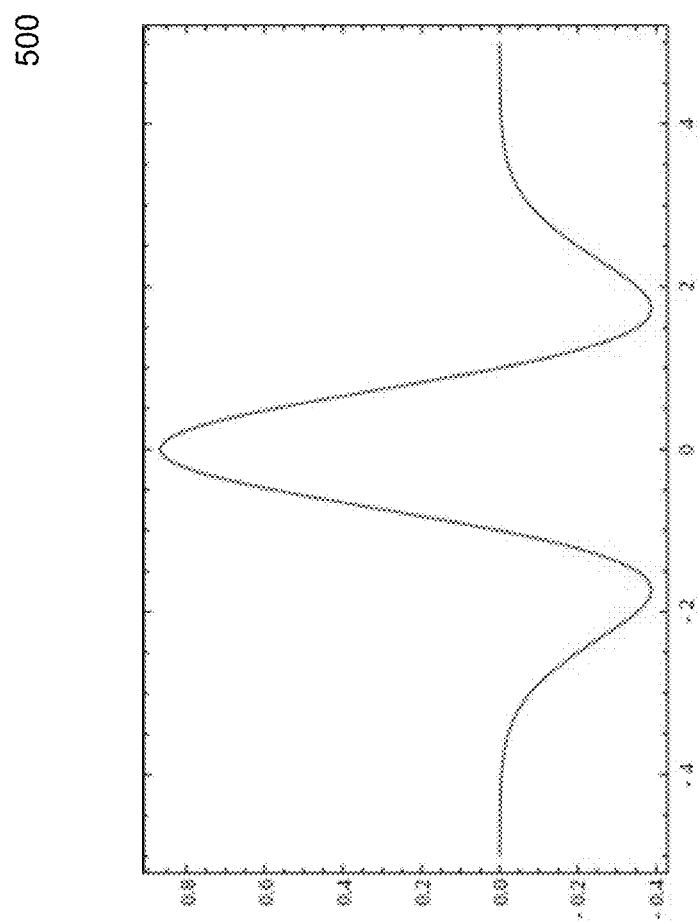
FIG. 5 shows a plot 500 of a Mexican Hat Wavelet according to embodiments of the present invention.

FIG. 5 shows a plot 500 of a Mexican Hat Wavelet according to embodiments of the present invention. The wavelet starts at zero, turns slightly negative, then more positive, and back to negative before returning to zero. Other wavelets can have more oscillations between positive and negative.

C. Determining Integrals (FFT)

In one embodiment, the integral involved in the transform and inverse transform can be determined numerically using Fourier analysis. The use of Fourier analysis to compute the integrals implicitly imposes periodic boundary conditions on the calculation, since it effectively treats it as a Fourier Series on a finite domain. Accordingly, the Fourier-based implementations effectively can impose periodic boundary conditions on truncated region of the time domain t for computing the integral.

To compute the integral, the input data signal can be Fourier transformed, e.g., using a discrete Fourier transform (DFT), such as a fast Fourier transform (FFT). The FFT uses a finite number of data points, which can correspond to the sampling points of the detector. The result provides the input data signal in frequencies, with a maximum frequency. Higher frequencies do not contribute. A Fourier transform is also taken of the particular localized function. The amplitudes of the transformed u( ) and ψ( ) can be multiplied for each of the finite set of frequencies used in the DFT, and then summed.

In another embodiment, the integral can be computed numerically by multiplying values of u(t) and values of the localized function. Thus, Fourier analysis would not need to be done. One may need to determine a time cutoff for computing the integral, i.e., using the cutoff instead of infinity.

V. Subtracting Out Certain Peak Data

As part of determining the background signal (i.e., the signal other than the peak of interest), certain coefficients of the 2D matrix are removed. The removed coefficients can correspond to coefficients associated with the peak of interest. For example, coefficients for functions that are centered in a time region of the peak can be set to zero (and that a cut function can be added later for these coefficients). Before removing certain coefficients from the 2D matrix, the time region for such coefficients is first determined.

The time region of the peak can be selected based on properties of the cluster of peaks. For example, a naive location associated with peak of interest can be determined.

A start and end of the naive peak can then be determined. In one implementation, all scales within the region are removed (also referred to as cut out).

Figure 6A:
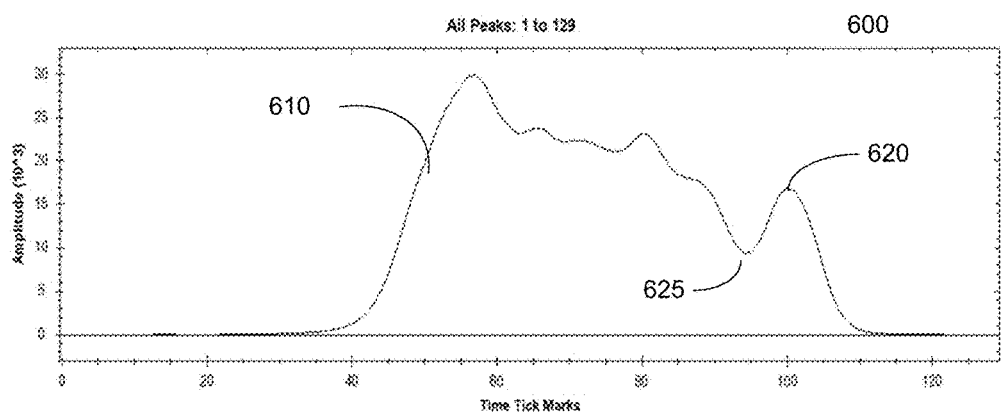
FIG. 6A shows a plot 600 of a cluster 610 of peaks according to embodiments of the present invention.

FIG. 6A shows a plot 600 of a cluster 610 of peaks according to embodiments of the present invention. In this example, peak 620 can be detected as lying between a trough 625 (local minimum) to the left and baseline (e.g., zero) value to the right. In one embodiment, trough 625 can be selected as the start of the time region corresponding to peak 620. The end of the time region could be selected in various ways. For example, the end of the time region can be selected such that peak 620 is centered in the time region. Thus, the distance between trough 625 and peak 620 would be equal to the distance between peak 620 and the end of the time region (also referred to as cut region).

Figure 6B:
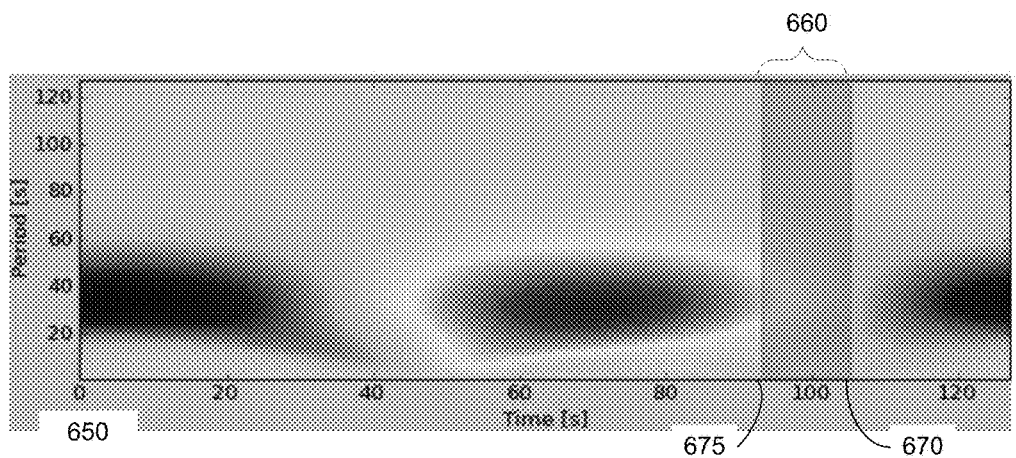
FIG. 6B shows a heat map 650 corresponding to cluster 610 according to embodiments of the present invention.

FIG. 6B shows a heat map 650 corresponding to cluster 610 according to embodiments of the present invention. A time region 660 is highlighted for cutting out coefficients from the 2D matrix. A start 675 of the cut region corresponds to trough 625. An end 670 defines the width of time region 660. In this example, the current region includes all scales. In another embodiment, not all scales be explicitly removed, e.g., wherein the corresponding coefficients are sufficiently small. In embodiments using FFTS, the range of the scales for the current region can be a power of two. The smallest power of two that contains the data can be used.

VI. Adding Tails of Other Peaks

Once the cut region has been identified in the old values of the coefficients removed, new values can be added. The new values correspond to a model of tails of other peaks. The new values represent everything except the peak of interest. The new values can be determined from a cut function, which may be computed once and then reused. In one embodiment, the cut function can provide a valley in the time space of the data signal, where a valley would correspond to the tails of neighboring peaks on both sides of the peak of interest.

A. Cut Function

In one embodiment, the cut function can receive a scale value i and a time value j for determining the corresponding coefficients for i and j. In one implementation, the cut function is:

$$\text{Cut}[i, j] = \left(\frac{\text{Min}}{A}\right) * \left(e^{-\left(B*\frac{i-\text{scaleCenter}}{\text{scaleWidth}}\right)^2 - \left(C*\frac{j-\text{timeCenter}}{\text{timeWidth}}\right)^2} - D\right),$$

where A, B, C, and D are regression parameters, i corresponds to the index for the scale factor in the two dimensional array, j corresponds to the index for time location in the two dimensional array, Min is the minimum value in the two-dimensional array, scaleWidth is a width of the scales covered by the two dimensional array, timeWidth is the width of the first time region, scaleCenter is a center of the width of the scales, and timeCenter is a center of the first time region.

Thus, in a 2D matrix of coefficients as shown in FIG. 6B, the value of i corresponds to a particular row in the 2D matrix, and the value of j corresponds to a particular column in the 2D matrix. The exponential (Gaussian) term allows for the modeling of the tales of the other peaks. The scale center can be taken as the middle of the range of scales that is used. For example, the center can be taken to be around 60 seconds in FIG. 6B. And, the scale width can be about 120 seconds. Thus, as the value i moves away from the scale center, the value of the cut function decreases, since the exponential term has a negative sign in the exponent. Similarly, as the value j moves away from the time center (e.g., about 99 seconds in FIG. 6B), the value of the cut function decreases, since the exponential term has a negative sign in the exponent. The time width is about from 92 seconds to about 106 seconds. The parameters B and C control the rate of decrease away from the centers.

The value of D can limit a maximum value for the cut function, and also allow setting for a minimum value. Similarly, the parameter A can define the range in values of the coefficients. The value of Min can be from the 2D matrix, and can be the minimum across all time for the input data signal.

In one embodiment, if the coefficients determined from the cut function were subject to an inverse transformation, the resultant signal would be a valley centered at the center of the time range. For example, an inverted Gaussian shape can be obtained. This shape can model tails of neighboring peaks on both sides of the peak of interest.

In some embodiments, the cut function can be applied to any cut range within the 2D map. The model does not depend on how many peaks are in the cluster or how close the peaks are to each other, except as conveyed by the time width. Various other functional forms for the cut function can be used. For example, an exponential decay can be used.

B. Using New Coefficients

Once the new values for the current region are determined, the new values can be placed into the 2D matrix to obtain an altered 2D matrix. The new values can directly replace the old values. A smoothing operation can be used to remove any discontinuities in the values the coefficients at the edges of the cut region. In one embodiment, the replacement with the new values can be followed by a low pass filter to smooth the discontinuous edges of the cut region.

C. Calculating Parameters

The parameters (e.g., A, B, C and D in example above) can be determined from an analysis of sample peaks signals that form a cluster. The underlying peak signals can be artificial signals that mimic isolated signals. In this manner, the actual peak signals are known, and thus parameters can be determined that provide accurate answers for various shapes of the underlying peak signal. For example, the parameters can be determined using wide width and narrow width calculations so that the parameters are applicable to a wide range of data. The wide width refers to underlying peak signals that are wide. The narrow width refers to underlying peak signals that are narrow.

A single regression calculation using wide width peaks can provide parameters that get about a fifth of all the peaks sufficiently accurate. Similarly, a separate regression calculation using narrow width peaks may provide accurate results for only a portion of peak signals that are encountered. In some embodiments, universally applicable parameters can be obtained by identifying parameter that are suitable for a range widths from wide to narrow for the underlying peaks. In this manner, the parameters can depend only on the width range, which is associated with the physical system, and on the set of localized functions (e.g., the range of scales used for the set). Thus, the cut function can be applied to any new data signal, provided the cut function is determined in a robust manner.

In one embodiment, the parameters can be determined by applying a nonlinear regression calculation to minimize the error for a suitably defined prototypical model incorporating the physical scales of the problem under consideration. For a defined physical system and problem, these values can be calculated once using an auxiliary calculation that is carried out. An optimization can be used to find the A, B, C and D that work the best for the range of examples used. This calculation can be slow, but once determined, these values are fixed thereafter. Thus, peak extraction using these fixed values can be very fast, e.g., much less than one second; few hundred milliseconds in some cases.

Figure 7A:
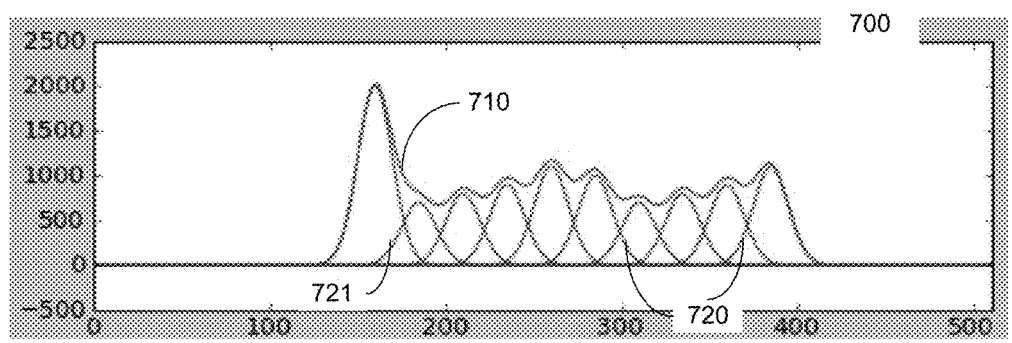
FIG. 7A shows a plot 700 of an artificial data signal 710 composed of underlying peaks 720 with a wide width of 14 according to embodiments of the present invention.

FIG. 7A shows a plot 700 of an artificial data signal 710 composed of ten underlying peaks 720 with a wide width of 14 according to embodiments of the present invention. Underlying peaks 720 overlap with each other. The number of peaks in a cluster are generally less than ten. Underlying peaks 720 have wide widths and are Gaussian functions in this example. Thus, artificial data signal 710 is an artificial overlapped function composed of a number of closely overlapped Gaussian functions. Underlying peaks 720 have varying amplitudes, and can be chosen to represent a typical range of peak sizes for the problem at hand (e.g., ddPCR). Each problem can have its own range of amplitudes, widths, and resolution for the scales and locations of the set of localized functions.

The task is to try to recover internal peaks from the total superposition of droplets in the artificial data signal 710. The recovered internal peaks should match underlying peaks 720, and the overlap of the recovered internal peaks should equal artificial data signal 710. Nonlinear regression is used to determine parameters (A,B,C,D) for a series of experiments. For each experiment, nonlinear regression is used over the artificial data signal 710 to minimize the error (differences) in simultaneously fitting all of the recovered internal peaks to determine the cut function parameters (A,B,C,D) by minimizing various properties, e.g., specific properties of one or more recovered peaks, such as specific differences of a recovered peak and an artificial data signal and/or underlying peaks.

Accordingly, in some embodiments, parameters of the cut function can be calculated using an artificial data signal (e.g. 710). The artificial data signal can be created from a first set of overlapping predetermined peak signals (e.g., underlying peaks 720). For each of the overlapping predetermined peak signals, a recovered peak can be determined by computing an artificial background signal (e.g., as described above) and subtracting the artificial background signal from the artificial data signal. Differences can be determined between the recovered peaks and the overlapping predetermined peak signals. The differences can be used in a regression analysis to determine the parameters of the cut function.

In some embodiments, the regression analysis could be a pointwise fit between the recovered internal peaks and the artificial data signal and/or the underlying peaks. In other embodiments, only certain properties of the recovered internal peaks may be used in the regression analysis.

Example properties to use in the optimization include: (a) height mismatch between each recovered internal peak and the artificial data signal; (b) width mismatch between underlying peaks (e.g., 720) and the recovered internal peaks; (c) location mismatch between peak locations of the underlying peaks and the recovered internal peaks; and (d) and any artifacts of a negative signal, e.g., an amount of negative values of a recovered peak. The parameters allow the extraction of the individual peak signals, e.g., according to method 300. These example properties can correspond to the differences of recovered peaks and overlapping predetermined peak signals that are minimized to determine new parameters.

Figure 8A:
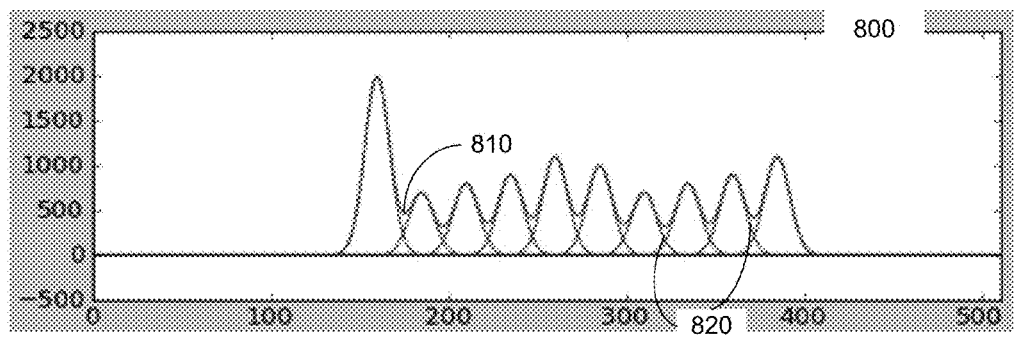
FIG. 8A shows a plot 800 of an artificial data signal 810 composed of underlying peaks 820 with a narrow width of 10 according to embodiments of the present invention.

FIG. 8A shows a plot 800 of an artificial data signal 810 composed of underlying peaks 820 with a narrow width of 10 according to embodiments of the present invention. In this example, each of the underlying peaks 820 can be seen in artificial data signal 810. Whereas, a hidden underlying peak 721 in FIG. 7A has a peak that is not readily identifiable in artificial data signal 710.

As mentioned above, each such experiment can have different regression parameters depending on the form of the underlying peaks. And, each such nonlinear regression can take up 15 minutes. As part of determining parameters that are applicable across a range, parameters are also determined for narrow widths. Table 1 shows the regression parameters that vary with width of the peaks, namely I narrow width 10 and a wide width 14.

TABLE 1

| Width | A | B | C | D |
|---|---|---|---|---|
| 10 | 0.872547 | 1.541077 | 1.078715 | 0.378669 |
| 4 | 0.926387 | 1.484917 | 1.257813 | 0.376679 |

To find universal parameters that will work with a range of underlying peaks, embodiments can average the regression parameters for the two cases, and use the average values as a new seed. The regression can proceed via iteration that optimizes the parameters using height mismatch, width mismatch, and negative artifacts (or other properties) for both sets of underlying peaks. Thus, for each iteration, the parameters can be updated to determine new recovered peaks and new differences, and the regression analysis can minimize the difference values for the specified properties.

The parameters from each regression can then be averaged again, and the average used as a new seed in the iteration. This process converges to the same set of parameters from both regressions, and thus are valid for both wide and narrow peaks, and all ranges in between. In another embodiment, the two width types of peaks can be included in a single cluster to which regression is performed. In yet another embodiment, a cluster for each width type can be used, but the differences for cluster can be combined into a single regression.

Accordingly, in some embodiments, the first set of overlapping predetermined peak signals can have a first width, and first set of parameters can be determined using the first set of overlapping predetermined peak signals. A second set of overlapping predetermined peak signals can be used to determine a second set of parameters. The second set of overlapping predetermined peak signals have a second width that is different than the first width. The first set of parameters and the second set of parameters can be averaged to obtain seed values for the parameters. The seed values can be used in a next regression iteration to determine new sets of parameters that are averaged to determine a new seed for the parameters. The computation of seed values can repeat until the first set of parameters and the second set of parameters converge to each other.

Figure 7B:
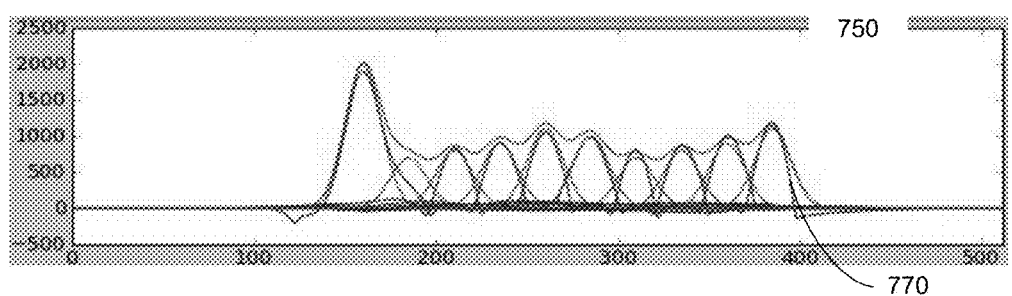
FIG. 7B is a plot 750 showing reconstructed internal peaks 770 according to embodiments of the present invention.

FIG. 7B is a plot 750 showing reconstructed internal peaks 770 according to embodiments of the present invention. Reconstructed internal peaks 770 are determined using the parameters obtained from the regression. The parameters are then used in method 300 to obtain reconstructed internal peaks 770. We see that all but hidden underlying peak 721 are effectively extracted. Hidden underlying peak 721 could be extracted by summing the extracted peaks and subtracting that sum from the data stream. What remains will be the hidden peak.

Figure 8B:
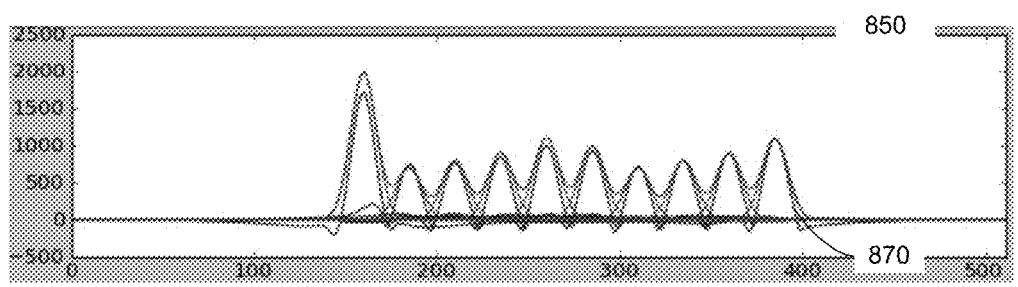
FIG. 8B is a plot 850 showing reconstructed internal peaks 870 according to embodiments of the present invention.

FIG. 8B is a plot 850 showing reconstructed internal peaks 870 according to embodiments of the present invention. Reconstructed internal peaks 870 match well with underlying peaks 820.

VII. Obtaining Peak

Using the cut function to determine the coefficients in the cut region, the background signal (altered 2D matrix) in a space of the localized functions is determined. Once the altered 2D array of coefficients is determined (i.e., after replacement using a cut function), the 2D array can be subject to the inverse transformation in equation (3). For a given time t, the coefficients in the altered 2D matrix are multiplied by corresponding localized way functions and integrated across the scale factors and time. This inverse transform projects in all the data signal in the space of the localized functions back into the original space of sampled data points vs. time. The result provides the background of the peak of interest. By calculating the background rather than the peak, embodiments can obtain the shift of the baseline due to the adjacent overlapped peaks.

The background signal is subtracted from the input data signal to get the recovered peak of interest. Embodiments do not need to model the peak, which allows the proximity induced distortions to be obtained. Embodiments can extract a single peak, and do not need to solve the whole problem as one would using multi peak nonlinear regression on a model.

Accordingly, to extract a peak that is assumed to have an arbitrary shape, embodiments can determine everything (background signal) except the peak of interest. In this manner, the effects of the adjacent peaks can be properly accounted for. And, by knowing the range of peak widths and amplitudes, the algorithm is universal for that range of peak widths and amplitudes.

VIII. Results

Figure 9:
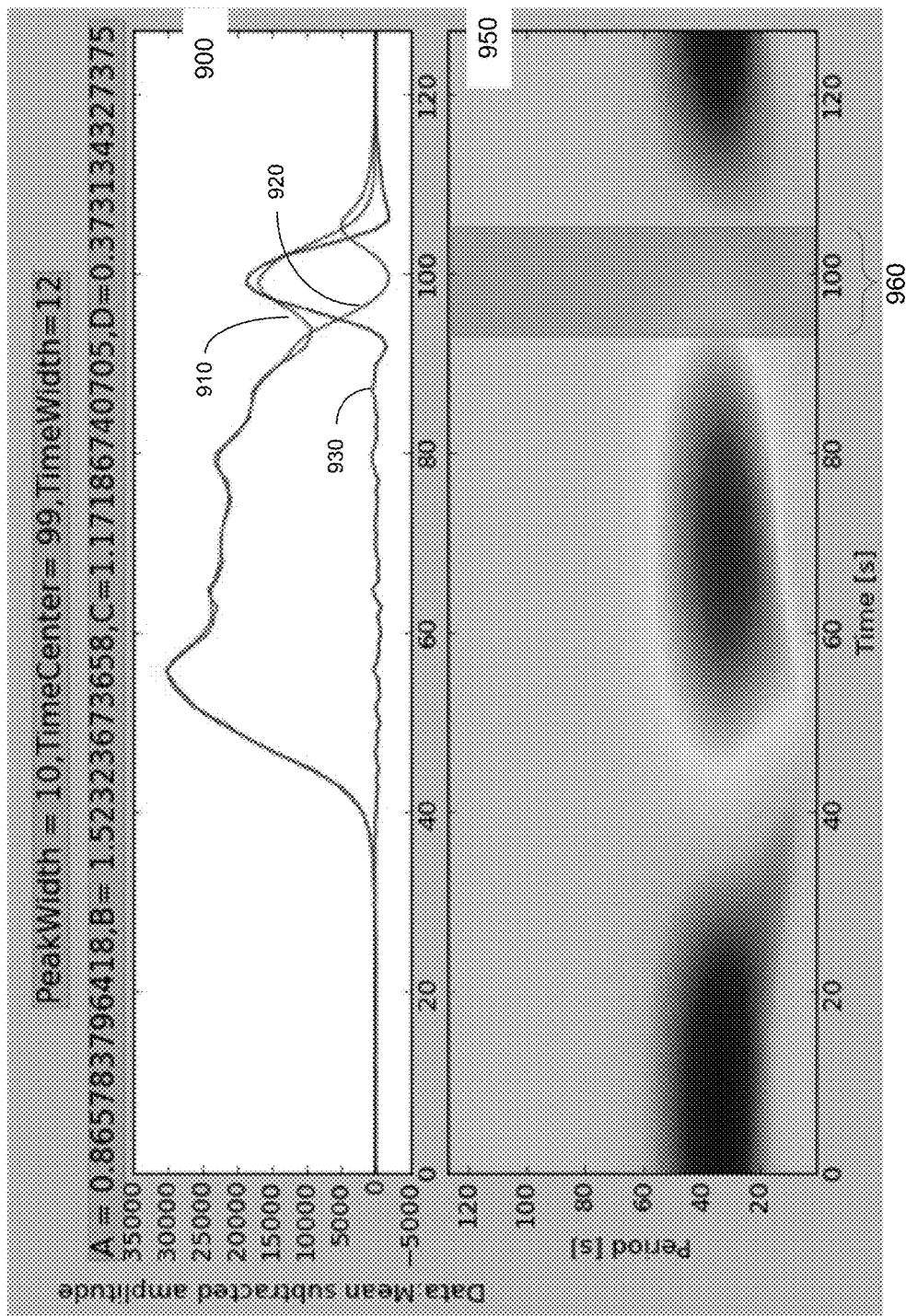
FIG. 9 shows a plot 900 and a heat map 950 illustrating a recovery of an internal peak according to embodiments of the present invention.

FIG. 9 shows a plot 900 and a heat map 950 illustrating a recovery of an internal peak according to embodiments of the present invention. Plot 900 shows an input data signal 910. A background signal 920 is determined using embodiments of the present invention. Background signal 920 is subtracted from input data signal 910 to obtain a recovered peak 930. Heat map 950 corresponds to input data signal 910. Cut region 960 is a region used to alter the coefficients of the 2D matrix that comprises heat map 950. Accordingly, cut region 960 corresponds to recovered peak 930.

Figure 10:
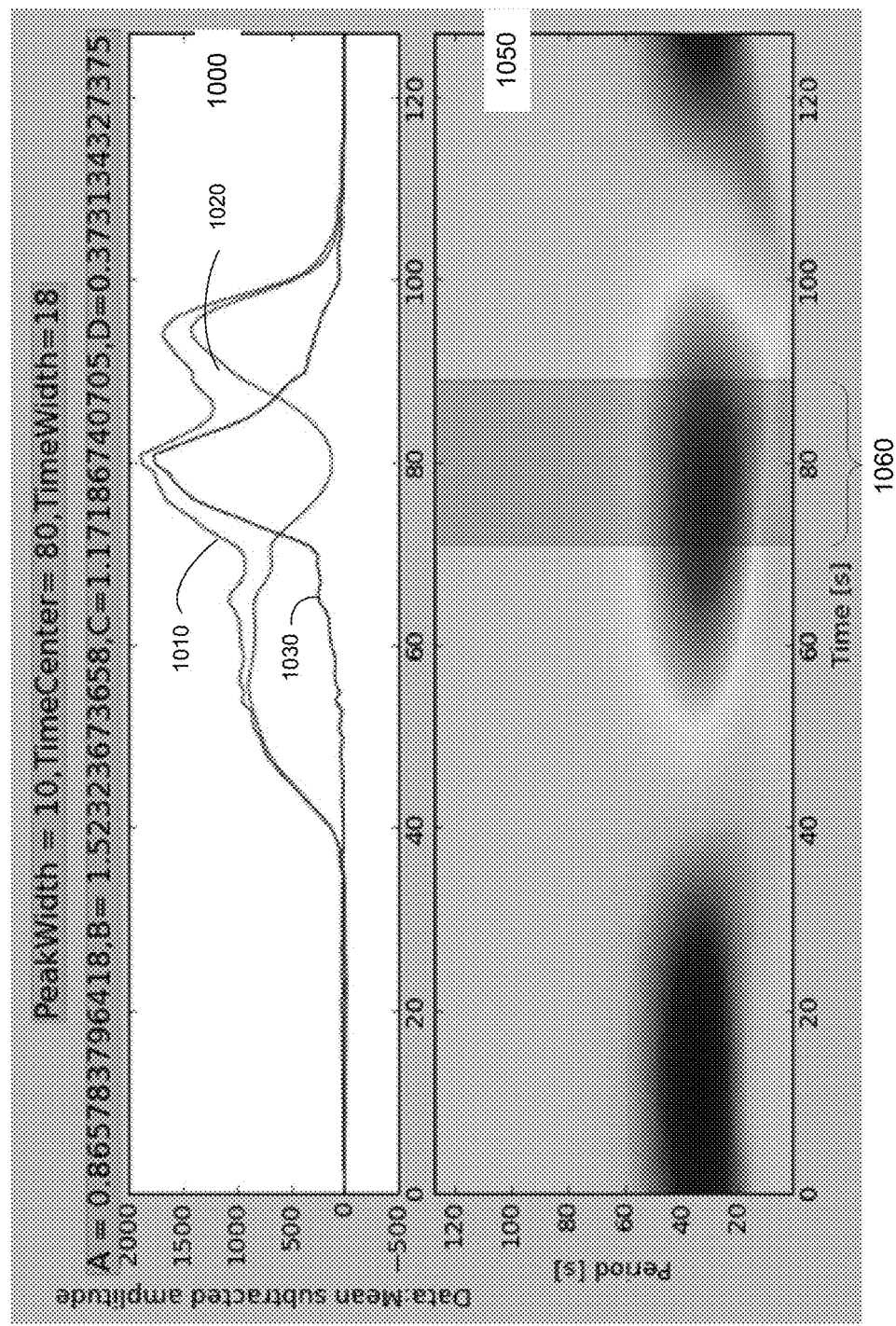
FIG. 10 shows a plot 1000 and a heat map 1050 illustrating a recovery of an internal peak according to embodiments of the present invention.

FIG. 10 shows a plot 1000 and a heat map 1050 illustrating a recovery of an internal peak according to embodiments of the present invention. Plot 1000 shows an input data signal 1010. A background signal 1020 is determined using embodiments of the present invention. Background signal 1020 is subtracted from input data signal 1010 to obtain a recovered peak 1030. Heat map 1050 corresponds to input data signal 1010. Cut region 1060 is a region used to alter the coefficients of the 2D matrix that comprises heat map 1050. Accordingly, cut region 1060 corresponds to recovered peak 1030. In this example using real data, recovered peak 1030 is not even close to Gaussian in shape. This illustrates a benefit of embodiments of the present invention in obtaining peak signals of arbitrary shape.

Embodiments can allow perfect reconstruction, or with truncation, imperfect reconstruction, i.e. compression. Embodiments can use only scale and relative location in order to carry out the analysis. In this manner, embodiments can avoid making any assumptions about the shape of the peak of interest.

IX. System

Figure 11:
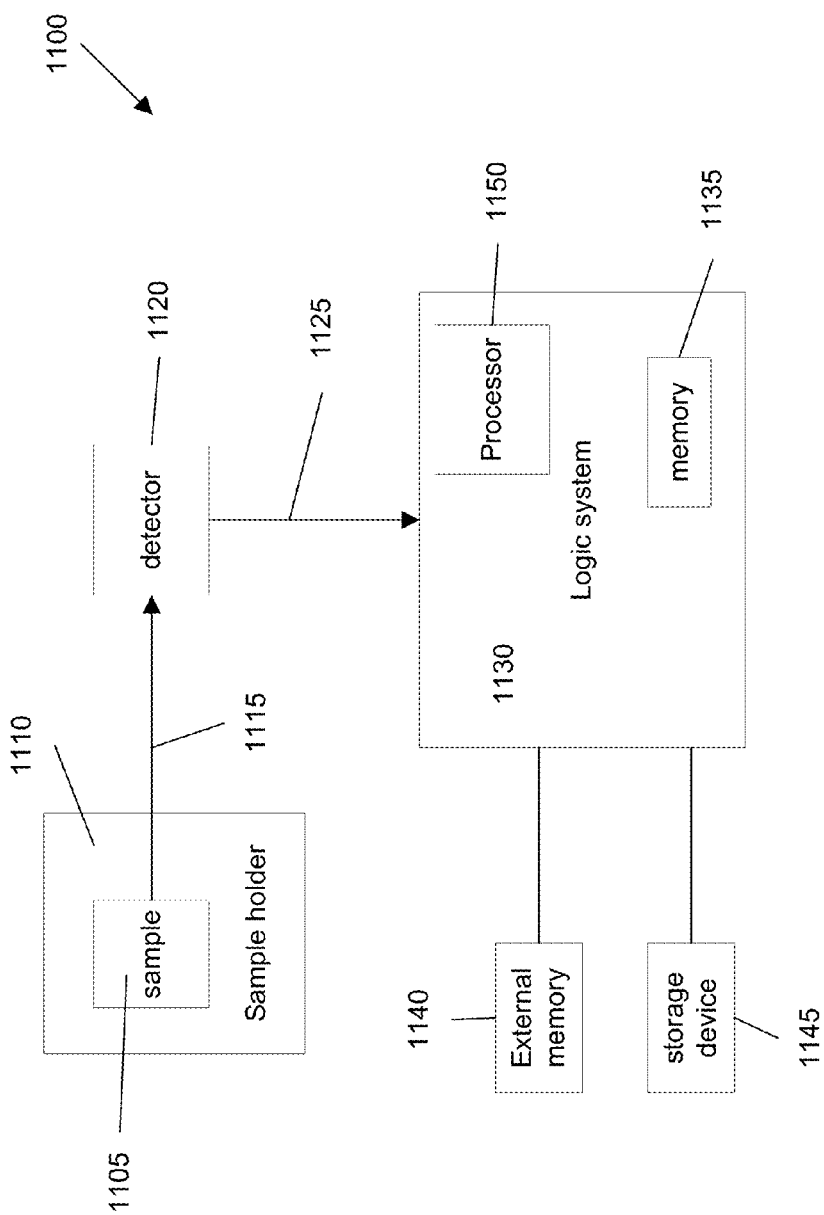
FIG. 11 illustrates a system 1100 according to an embodiment of the present invention.

FIG. 11 illustrates a system 1100 according to an embodiment of the present invention. The system as shown includes a sample 1105, such as a DNA molecule or a droplet containing DNA, within a sample holder 1110. An example of a sample holder can be a tube through which a droplet moves or a nanopore through which a DNA molecule moves. A physical characteristic 1115, such as a fluorescence intensity value, from the sample is detected by detector 1120. Detector can take a measurement at intervals (e.g., periodic intervals) to obtain data points that make up a data signal. In one embodiment, an analog to digital converter converts an analog signal from the detector into digital form at a plurality of times. A data signal 1125 is sent from detector 1120 to logic system 1130. Data signal 1125 may be stored in a local memory 1135, an external memory 1140, or storage device 1145.

Logic system 1130 may be, or may include, a computer system, ASIC, microprocessor, etc. It may also include or be coupled with a display (e.g., monitor, LED display, etc.) and a user input device (e.g., mouse, keyboard, buttons, etc.). Logic system 1130 and the other components may be part of a stand-alone or network connected computer system, or they may be directly attached to or incorporated in a thermal cycler device. Logic system 1130 may also include optimization software that executes in a processor 1150

Figure 12:
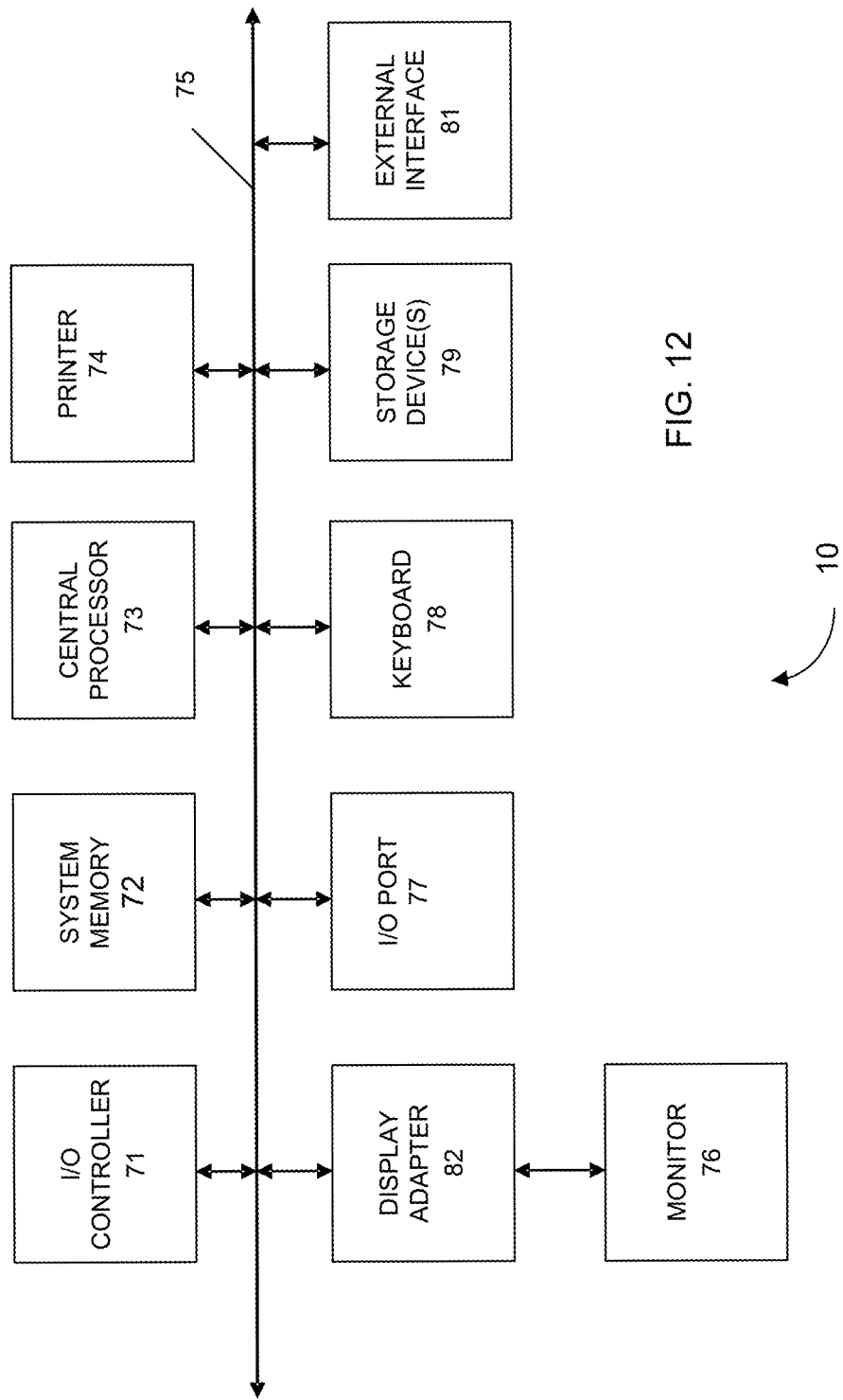
FIG. 12 shows a block diagram of an example computer system 10 usable with system and methods according to embodiments of the present invention.

Any of the computer systems mentioned herein may utilize any suitable number of subsystems. Examples of such subsystems are shown in FIG. 12 in computer apparatus 10. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 12 are interconnected via a system bus 75. Additional subsystems such as a printer 74, keyboard 78, storage device(s) 79, monitor 76, which is coupled to display adapter 82, and others are shown. Peripherals and input/output (I/O) devices, which couple to I/O controller 71, can be connected to the computer system by any number of means known in the art such as input/output (I/O) port 77 (e.g., USB, FireWire®). For example, I/O port 77 or external interface 81 (e.g. Ethernet, Wi-Fi, etc.) can be used to connect computer system 10 to a wide area network such as the Internet, a mouse input device, or a scanner. The interconnection via system bus 75 allows the central processor 73 to communicate with each subsystem and to control the execution of instructions from system memory 72 or the storage device(s) 79 (e.g., a fixed disk, such as a hard drive or optical disk), as well as the exchange of information between subsystems. The system memory 72 and/or the storage device(s) 79 may embody a computer readable medium. Any of the data mentioned herein can be output from one component to another component and can be output to the user.

A computer system can include a plurality of the same components or subsystems, e.g., connected together by external interface 81 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g. an application specific integrated circuit or field programmable gate array) and/or using computer software with a generally programmable processor in a modular or integrated manner. As used herein, a processor includes a multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C#, Objective-C, Swift, or scripting language such as Perl or Python using, for example, conventional or object-oriented techniques. The software code may be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

A recitation of "a", "an" or "the" is intended to mean "one or more" unless specifically indicated to the contrary. The use of "or" is intended to mean an "inclusive or," and not an "exclusive or" unless specifically indicated to the contrary.

All patents, patent applications, publications, and descriptions mentioned here are incorporated by reference in their entirety for all purposes. None is admitted to be prior art.

What is claimed is:

1. A method of identifying a first peak signal corresponding to a first part of a biological sample from among other peak signals of other parts of the biological sample, the biological sample including a plurality of droplets that contain nucleic acids and correspond to different parts of the biological sample, the method comprising, at a computer system:

receiving a data signal from a droplet digital polymerase chain reaction (ddPCR) experiment involving the biological sample, the data signal having an amplitude that varies over time, wherein the data signal comprises a plurality of overlapped peaks at different times;

transforming the data signal to obtain a two-dimensional array of coefficients corresponding to localized functions, each coefficient corresponding to a localized function having a time location and a scale factor;

identifying a first time region corresponding to a first peak of the first peak signal;

removing the coefficients of the two-dimensional array corresponding to localized functions with time locations within the first time region;

determining new coefficients for the two-dimensional array using a cut function that models tails of other peak signals;

using the new coefficients to obtain an altered two-dimensional array;

performing an inverse transform of the altered two-dimensional array to obtain a background signal;

subtracting the background signal from the data signal to obtain the first peak signal corresponding to the first part of the biological sample; and determining a presence or absence of a nucleic acid sequence in the first part of the biological sample based on the first peak signal.

2. The method of claim 1, further comprising calculating parameters of the cut function by:

creating an artificial data signal from a first set of overlapping predetermined peak signals;

for each of the overlapping predetermined peak signals, computing a recovered peak by computing an artificial background signal and subtracting the artificial background signal from the artificial data signal;

determining differences between the recovered peaks and the overlapping predetermined peak signals; and using the differences in a regression analysis to determine the parameters of the cut function.

3. The method of claim 2, wherein the parameters are updated to determine new recovered peaks and new differences, and wherein the regression analysis minimizes the differences.

4. The method of claim 2, wherein the differences include at least one of: a height mismatch, a width mismatch, a location mismatch, and negative values of a recovered peak.

5. The method of claim 2, wherein the first set of overlapping predetermined peak signals have a first width and a first set of parameters is determined using the first set of overlapping predetermined peak signals, the method further comprising:
using a second set of overlapping predetermined peak signals to determine a second set of parameters, the second set of overlapping predetermined peak signals having a second width that is different than the first width;
averaging the first set of parameters and the second set of parameters to obtain seed values for the parameters;
using the seed values in a next regression iteration to determine new sets of parameters that are averaged to determine a new seed for the parameters; and
repeating computation of seed values until the first set of parameters and the second set of parameters converge to each other.

6. The method of claim 1, wherein the cut function is defined as:

$$\text{Cut}[i, j] = \left(\frac{\text{Min}}{A}\right) * \left(e^{-\left(B*\frac{i-scaleCenter}{scaleWidth}\right)^2 - \left(C*\frac{j-timeCenter}{timeWidth}\right)^2} - D\right),$$

where A, B, C, and D are regression parameters, i corresponds to a scale index for the scale factor in the two-dimensional array, j corresponds to a time index for the time location in the two-dimensional array, Min is a minimum value in the two-dimensional array, scaleWidth is a width of the scale factors covered by the two-dimensional array, timeWidth is a width of the first time region, scaleCenter is a center of the width of the scale factors, and timeCenter is a center of the first time region.

7. The method of claim 1, wherein transforming the data signal to obtain a particular coefficient of the two-dimensional array includes:
computing a convolution of the data signal and a particular localized function centered at a time t and having a scale factor a.

8. The method of claim 7, wherein computing the convolution includes:
calculating a first discrete transform of the data signal to obtain a first set of data points;
calculating a second discrete transform of the particular localized function to obtain a second set of data points; and
multiplying data points of the first set with corresponding data points of the second set and summing to obtain a result of the convolution.

9. The method of claim 8, wherein the first discrete transform and the second discrete transform are Fourier transforms.

10. The method of claim 1, wherein identifying the first time region includes:
identifying a first boundary of the first time region to be a local minimum between the first peak and a second peak.

11. The method of claim 1, wherein a scale factor corresponds to a period or frequency of the localized function.

12. The method of claim 1, wherein the localized functions are wavelets.

13. The method of claim 1, further comprising:
determining an amount of the nucleic acid sequence in the biological sample based on a presence or absence of the nucleic acid sequence in each of the plurality of droplets.

14. A computer product comprising a non-transitory computer readable medium storing instructions, that when executed on one or more processors of a computer system, perform identifying a first peak signal corresponding to a first part of a biological sample from among other peak signals of other parts of the biological sample, the biological sample including a plurality of droplets that contains nucleic acids and corresponds to different parts of the biological sample, the instructions comprising:
receiving a data signal from a droplet digital polymerase chain reaction (ddPCR) experiment involving the biological sample, the data signal having an amplitude that varies over time, wherein the data signal comprises a plurality of overlapped peaks at different times;
transforming the data signal to obtain a two-dimensional array of coefficients corresponding to localized functions, each coefficient corresponding to a localized function having a time location and a scale factor;
identifying a first time region corresponding to a first peak of the first peak signal;
removing the coefficients of the two-dimensional array corresponding to localized functions with time locations within the first time region;
determining new coefficients for the two-dimensional array using a cut function that models tails of the other peak signals;
using the new coefficients to obtain an altered two-dimensional array;
performing an inverse transform of the altered two-dimensional array to obtain a background signal;
subtracting the background signal from the data signal to obtain the first peak signal corresponding to the first part of the biological sample; and
determining a presence or absence of a nucleic acid sequence in the first part of the biological sample based on the first peak signal.

15. The computer product of claim 14, further comprising:
one or more processors, wherein the one or more processors are communicably coupled to the non-transitory computer readable medium;
a sample holder configured to hold the biological sample; and
a detector configured to detect the data signal in the ddPCR experiment involving the biological sample, wherein the detector is communicably coupled with the one or more processors.

16. The computer product of claim 14, wherein the instructions further comprise calculating parameters of the cut function by:
creating an artificial data signal from a first set of overlapping predetermined peak signals;
for each of the overlapping predetermined peak signals, computing a recovered peak by computing an artificial background signal and subtracting the artificial background signal from the artificial data signal;
determining differences between the recovered peaks and the overlapping predetermined peak signals; and
using the differences in a regression analysis to determine the parameters of the cut function.

17. The computer product of claim 14, wherein the cut function is defined as:

$$Cut[i,j] = \left(\frac{Min}{A}\right) * \left(e^{-\left(B*\frac{i-scaleCenter}{scaleWidth}\right)^2 - \left(C*\frac{j-timeCenter}{timeWidth}\right)^2} - D\right),$$

where A, B, C, and D are regression parameters, i corresponds to a scale index for the scale factor in the two-dimensional array, j corresponds to a time index for the time location in the two-dimensional array, Min is a minimum value in the two-dimensional array, scaleWidth is a width of the scale factors covered by the two-dimensional array, timeWidth is a width of the first time region, scaleCenter is a center of the width of the scale factors, and timeCenter is a center of the first time region.

18. The computer product of claim 14, wherein transforming the data signal to obtain a particular coefficient of the two-dimensional array includes:
  computing a convolution of the data signal and a particular localized function centered at a time t and having a scale factor a.

19. The computer product of claim 14, wherein identifying the first time region includes:
  identifying a first boundary of the first time region to be a local minimum between the first peak and a second peak.

20. The computer product of claim 14, wherein the instructions further comprise:
  determining an amount of the nucleic acid sequence in the biological sample based on a presence or absence of the nucleic acid sequence in each of the plurality of droplets.

\* \* \* \* \*